US00PP19245P2

(12) United States Plant Patent
Vermeulen

(10) Patent No.: US PP19,245 P2
(45) Date of Patent: Sep. 16, 2008

(54) ***DRACAENA* PLANT NAMED 'PV200604'**

(50) Latin Name: *Dracaena steudneri*
Varietal Denomination: PV200604

(76) Inventor: Herman Vermeulen, Minnezang 14 3210, Linden (BE)

( * ) Notice: Subject to any disclaimer, the term of this patent is extended or adjusted under 35 U.S.C. 154(b) by 0 days.

(21) Appl. No.: 11/653,148

(22) Filed: Jan. 12, 2007

(51) Int. Cl.
*A01H 5/00* (2006.01)

(52) U.S. Cl. ..... Plt./383
(58) Field of Classification Search ..... Plt./383
See application file for complete search history.

*Primary Examiner*—Annette H Para
*Assistant Examiner*—S. B. McCormick-Ewoldt

(57) ABSTRACT

A new cultivar of *Dracaena* plant named 'PV200604', that is characterized by wide dark green leaves and a green stem.

1 Drawing Sheet

Botanical classification: *Dracaena steudneri.*
Variety denomination: 'PV200604'.

BACKGROUND OF THE INVENTION

The present invention relates to a new and distinct cultivar of *Dracaena* plant botanically known as *Dracaena steudneri* and hereinafter referred to by the cultivar name 'PV200604'.

The new cultivar was discovered in 2003 in a cultivated area of La Balsa, Costa Rice. 'PV200604' was discovered as a naturally occurring whole plant mutation in a bed of unnamed *Dracaena steudneri* plants. 'PV200604' was discovered as single plant.

Asexual reproduction by cuttings of the new cultivar 'PV200604' first occurred in 2003 in La Balsa, Costa Rica.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dracaena* cultivar 'PV200604'. These traits in combination distinguish 'PV200604' as a new and distinct cultivar.

1. *Dracaena* 'PV200604' exhibits wide dark green leaves.
2. *Dracaena* 'PV200604' exhibits a green stem.

The new cultivar 'PV200604' is distinguishable from typical *Dracaena steudneri* plants of the species and from the bed of unnamed *Dracaena steudneri* plants in which 'PV200604' was found by the following characteristics:

1. 'PV200604' has darker green leaves.
2. 'PV200604' has wider leaves.
3. 'PV200604' has a green stem.

BRIEF DESCRIPTION OF THE DRAWING

The accompanying photograph illustrates the distinguishing traits of *Dracaena* 'PV200604'. The plant in the photograph shows an overall view of a 18 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Dracaena* cultivar named 'PV200604'. Data was collected in Boskoop, The Netherlands from plants grown in Linden, Belgium. The plants were 18 month old greenhouse grown plants in 19 cm diameter containers. The temperature ranged from 19 to 30° Centigrade. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'PV200604' has not been tested under all possible conditions and phenotypic differences may be observed with variations in environmental, climatic, and cultural conditions, however, without any variance in genotype.

Botanical classification: *Dracaena steudneri* 'PV200604'.
Parentage: 'PV200604' was discovered as a naturally occurring whole plant mutation in a bed of unnamed *Dracaena steudneri* plants.
Annual or perennial: Perennial.
Use: Ornamental.
Vigor: Moderate.
Growth habit: Upright.
Plant shape: Inverted triangle.
Suitable container size: 17 cm. container.
Height: Average 58.7 cm. in height.
Width: Average 40.7 cm. in width.
Hardiness: USDA Zone 10.
Growth rate: Approximately 4 cm. per month.
Propagation: Cuttings.
Time to initiate roots: Approximately 29 days to produce roots on an initial cutting.
Time to produce a rooted cutting or liner: Approximately 35 days.
Crop time: Approximately 12 months to produce a finished plant from a rooted cutting.
Root system: Fine and fibrous.
Root color: 166B.

Stem:

*Stem length.*—*Average* 13.8 cm.

*Stem diameter.*—Average 1.2 cm.

*Stem strength.*—Very strong.

*Stem color.*—146D; older stems 139A with some blotches of 143A.

*Stem pubescence.*—Absent.

*Internode length.*—Average 1.4 cm.

*Stem shape.*—Round.

*Stem surface.*—Smooth, with leaf scars along the stem.

Branches:

*Branch number.*—Average 2.

*Branch length.*—Average 13.8 cm.

*Branch diameter.*—Average 1.2 cm.

*Branch color.*—146D.

Foliage:

*Texture.*—Smooth, glossy, slightly leathery.

*Leaf arrangement.*—Alternate.

*Compound or single.*—Single.

*Quantity of leaves.*—Average 8.

*Leaf shape.*—Lorate.

*Leaf apex.*—Apiculate.

*Leaf base.*—Sheathing.

*Leaf length.*—Average 24.1 cm. in length.

*Leaf width.*—Average 5.8 cm. in width.

*Pubescence.*—Absent.

*Leaf margin.*—Entire.

*Vein pattern.*—Parallel.

*Young leaf color* (*upper surface*).—Between 137A and 139A; base between 143A and 144A.

*Young leaf color* (*lower surface*).—137C; base 138B.

*Mature leaf color* (*upper surface*).—Between 137A and 139A.

*Mature leaf color* (*lower surface*).—137C.

*Vein color upper surface.*—Varies from 137A to 139A.

*Vein color lower surface.*—137C.

*Leaf attachment.*—Sessile.

*Durability of foliage to stress.*—High.

Flower: Flowering has not been observed.

Disease and pest resistance: 'PV200604' has not been observed for disease or pest resistance.

What is claimed is:

1. A new and distinct variety of *Dracaena* plant named 'PV200604' as described and illustrated.

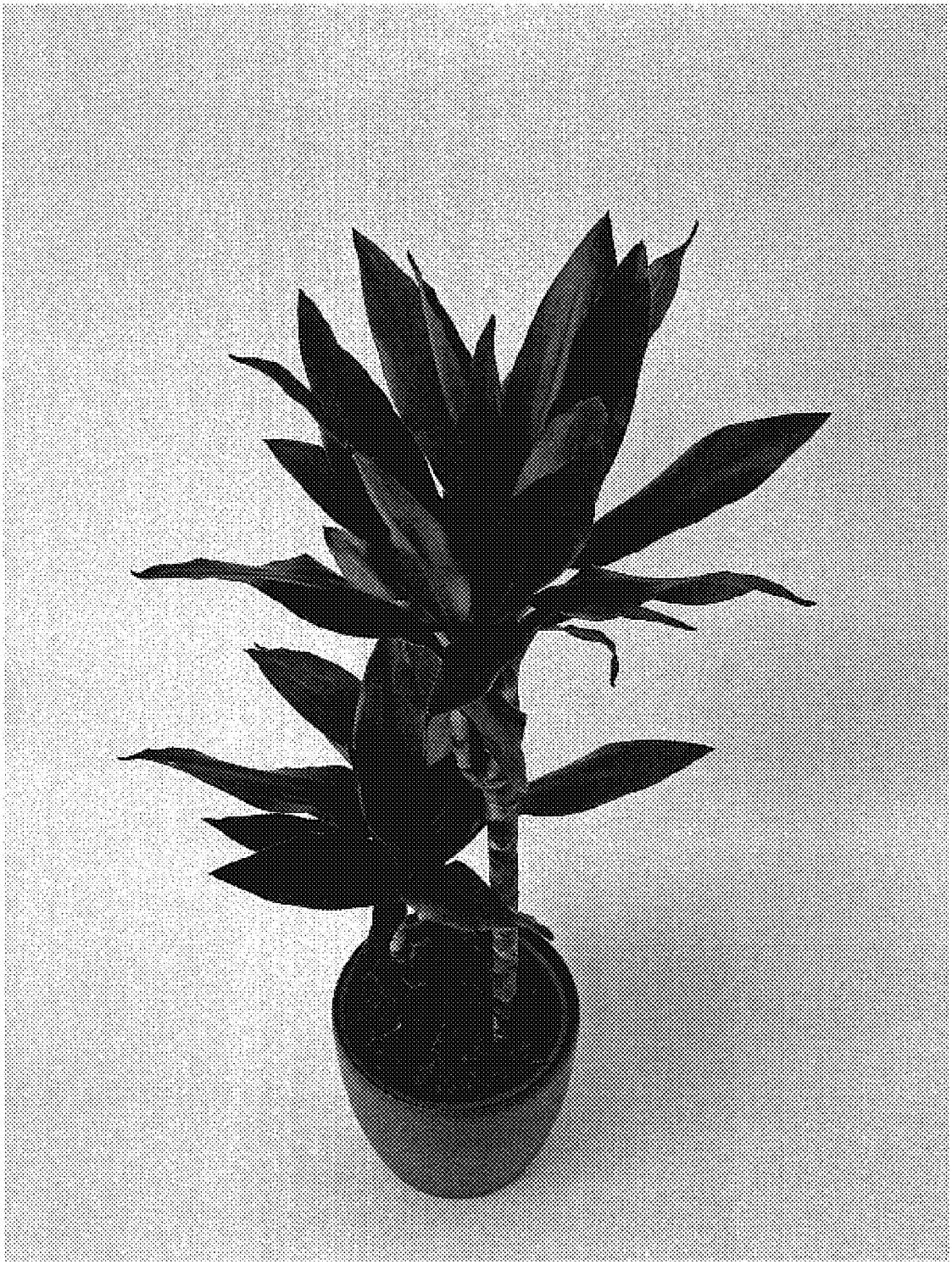

* * * * *